US 6,741,673 B2

(12) United States Patent
Kamenetsky et al.

(10) Patent No.: US 6,741,673 B2
(45) Date of Patent: May 25, 2004

(54) MAMMOGRAPHY DEVICE AND METHOD UTILIZING OPTIMALLY CURVED SUPPORT PLATE CONFIGURATION FOR ACCURACY IN IMAGING AND DIAGNOSIS

(76) Inventors: Mikhail Kamenetsky, 8814 Bay Pkwy., Apt. 2J, Brooklyn, NY (US) 11214; Aron Pesok, 86 Bay 26th St., Apt. C1, Brooklyn, NY (US) 11214; Marina Pervak, 40 Ilyicha Avenue, apt. 13, Donetsk (UA), 83003; Aleksey Kamenetsky, 312 Links Dr. West., Oceanside, NY (US) 11572; Yelena Vidgop, 53 Corona Ct., Old Bridge, NJ (US) 08857

( * ) Notice: Subject to any disclaimer, the term of this patent is extended or adjusted under 35 U.S.C. 154(b) by 49 days.

(21) Appl. No.: 10/213,256

(22) Filed: Aug. 6, 2002

(65) Prior Publication Data

US 2004/0028176 A1 Feb. 12, 2004

(51) Int. Cl.⁷ .................................................. A61B 6/04
(52) U.S. Cl. .......................... 378/37; 378/208; 128/915
(58) Field of Search .................... 378/37, 208; 128/915

(56) References Cited

U.S. PATENT DOCUMENTS

| 4,901,351 A | | 2/1990 | Tanaka et al. ................. 380/15 |
| 4,905,269 A | * | 2/1990 | Mosby ......................... 378/182 |
| 4,943,986 A | * | 7/1990 | Barbarisi ....................... 378/37 |
| 4,943,991 A | * | 7/1990 | Mosby ......................... 378/182 |
| 5,170,419 A | | 12/1992 | Johansson et al. ............. 378/37 |
| 5,506,877 A | | 4/1996 | Niklason et al. ............... 378/37 |
| 5,526,394 A | | 6/1996 | Siczek et al. .................. 378/37 |
| 5,712,890 A | | 1/1998 | Spivey et al. .................. 378/37 |
| 6,005,911 A | | 12/1999 | Cheung ........................ 378/37 |
| 6,064,715 A | | 5/2000 | Sklebitz et al. ............... 378/37 |
| 6,195,580 B1 | | 2/2001 | Grable ........................ 600/473 |
| 6,208,708 B1 | | 3/2001 | Hoheisel et al. ............... 378/37 |
| 6,292,531 B1 | | 9/2001 | Hsieh ........................... 378/37 |
| 6,296,386 B1 | | 10/2001 | Heidsieck et al. .......... 378/189 |
| 6,326,625 B1 | | 12/2001 | Zur ........................ 250/370.09 |
| 6,633,626 B2 | * | 10/2003 | Trotter et al. .................. 378/62 |

* cited by examiner

Primary Examiner—Craig E. Church
Assistant Examiner—Jurie Yun
(74) Attorney, Agent, or Firm—Chadbourne & Parke, LLP (57) ABSTRACT

An improved x-ray mammography diagnostic apparatus with a digital detector forming a preferably rotatable subject table having a first concave curved surface formed by several arcs with different radii on one side of the table and another concave curved surface formed by several arcs with different radii on either adjacent or opposite side of the same table, these two curved surfaces allowing to accommodate curvature of the human breast and curvature of the rib cage below the breast of each patient and permitting to take a complete x-ray reading and detection of all areas of the human breast under examination, particularly at all points of connection with the rib cage wall and in the axilla area. The second concave curved surface is configured to fittingly accommodate the curvature of individuals with different bodily dimensions than those that could be accommodated by the first concave curved surface.

23 Claims, 6 Drawing Sheets

MAMMOGRAPHY DEVICE AND METHOD UTILIZING OPTIMALLY CURVED SUPPORT PLATE CONFIGURATION FOR ACCURACY IN IMAGING AND DIAGNOSIS

FIELD OF THE INVENTION

The present invention pertains in general to the x-ray mammography apparatus and method. It particularly relates to the detector device utilized with conventional and digital mammography x-ray devices in order to improve the accuracy of the reading and diagnosis.

BACKGROUND OF THE INVENTION

As the current medical profession battles to find a cure for breast cancer, x-ray mammography is widely utilized for the screening and diagnosis of breast cancer for millions of women throughout the world. With millions of women diagnosed with breast cancer, the ability to detect and diagnose the incidence of breast cancer as early as possible is absolutely essential. The mistakes or failures in detection end up barring the possibility of early treatment for breast cancer in the most effective manner, requiring expensive and significantly more dangerous surgical and other procedures and even causing death for some patients. In addition, the so-called "false positives" are very prevalent with current mammography devices and systems, which often translates into unnecessary costs (for biopsy tests, etc.) and patient trauma.

Mammography, which usually means the radiological examination of the human breast, is typically performed with x-ray or other film/screen techniques. The film screen x-ray mammography technique involves directing a beam of x-ray through the breast onto a phosphor screen, which converts each x-ray photon into a number of visible photons that expose a sheet of photosensitive film, which is located in a close proximity to the phosphor, thereby forming a latent image of the x-ray pattern. The photographic film is developed to transform the latent image into a visible analog representation of the x-ray pattern.

While still widely used throughout the word, the film-screen mammography technique is known to have some shortcomings and limitations. For example, one shortcoming of conventional x-ray mammography is that the range of contrast of the photosensitive film is limited and fails to display the entire range of contrast in the examined human breast. Because the gray-level of x-ray film has a sigmoidal response as a function of exposure, it causes some difficulties in differentiating the contrast at the extremes of the exposure range (in the most radiodense and radiolucent areas of the photo image), thereby complicating analysis and diagnosis of soft tissue masses in those areas.

A more precise approach to the diagnosis of breast cancer had been proposed with the advent of digital mammography techniques, where the phosphor and film detector is replaced with a digital image detector, which provides a much wider range of contrast than photosensitive film, and where the contrast response is linear over the entire contrast range. This allows the digital detector of the mammography device to differentiate among very subtle variations in attenuation of x-rays as they pass through the soft tissue of human breast.

Figure 1:
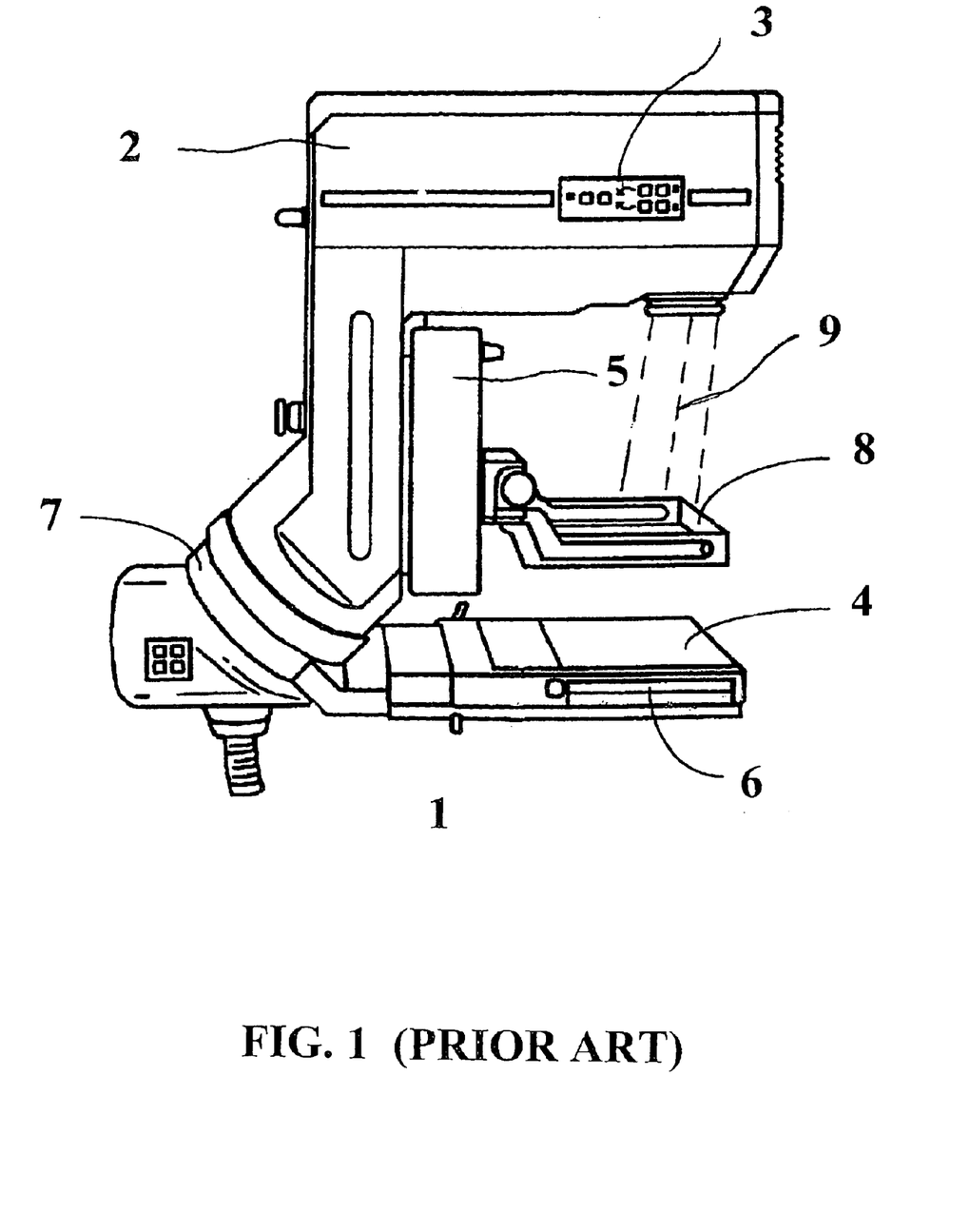
FIG. 1 is a side view of an x-ray mammography device that is currently utilized for detection and diagnosis of breast cancer.

As shown in FIG. 1, a typical mammography apparatus 1 that is commonly used today has an x-ray housing 2 that carries an x-ray arrangement 3 (or an x-ray tube), a subject table 4 and a compression mechanism 5, with compression plate 8. A detector cassette 6, with photosensitive film can be inserted into subject table 4 in the horizontal direction. The housing 2 can be mounted on a rotary arm 7 that is rotatably attached to a movable stand (not shown), allowing the x-ray housing to rotate in order to be able to take x-ray measurements from the side. A more detailed description of a conventional x-ray apparatus is given in the U.S. Pat. No. 6,208,708 and U.S. Pat. No. 5,170,419, the disclosure of which is incorporated herein by reference.

It is also known in the art that a detector cassette itself may serve as a subject table, in which case the compression plate 8 presses the examination subject against the upper surface of the cassette holder when the x-ray beam 9 is emitted by the x-ray tube through the subject breast toward the detector cassette.

Figure 2:
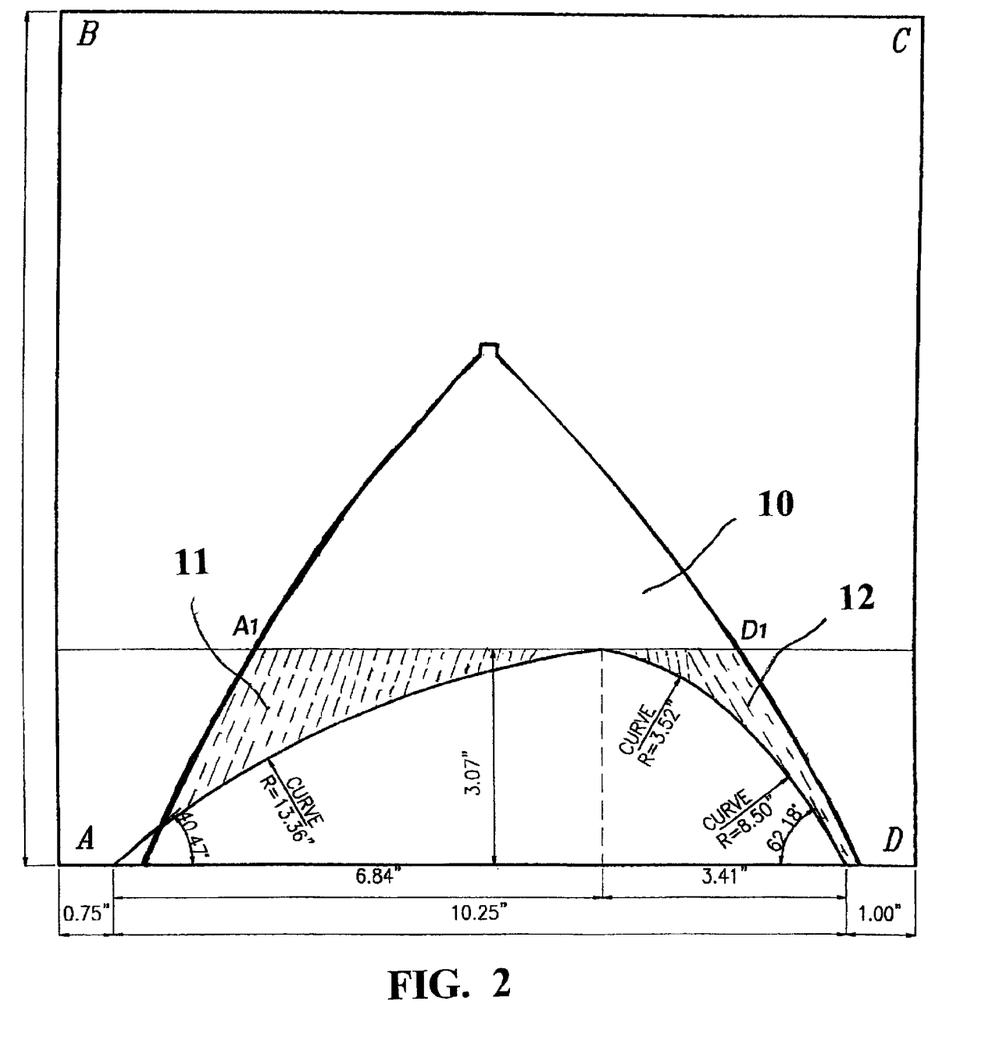
FIG. 2 is a diagram of a human breast, depicting areas at the opposite far corners of the junction of the breast and the rib cage, that are often missed or improperly detected during the x-ray mammography test when a subject table with straight rectangular edges is utilized.

One significant shortcoming of the typical x-ray mammography devices that are currently utilized and known in the art, which is common to both the film screen x-ray devices and those that utilize digital detectors, is that the shape of the subject table 4 and the detector cassette 8 (or detector plate in digital mammography devices) is always rectangular. Because the human breast, rib cage below the breast and axillia areas are not linear, when the subject breast is compressed between the subject table and the compression plate and the x-ray beams transmitted, detected and imaged, certain portions 11 or 12 at the far corners of the junction of the breast 10, as shown in FIG. 2 are not properly detected and imaged, thereby creating a potential for misdiagnosis or requiring that the diagnostic mammography procedure be repeated, thus, subjecting the individual to additional x-ray exposure and increasing overall cost of mammography procedures in the aggregate. In many cases, the rectangular cassettes (or digital detectors) also fail to properly image the axilla area, and, therefore, fail to detect cancerous growth in that area, putting the patient's life at risk. If a cassette with a concave curved surface, formed by one arc with one radius, is utilized in a mammography cassette, the curved surface of such cassette would not be able to accommodate left and right curvature of human breast and curvature of the rib cage below the breast. Thus such cassette would not allow a complete x-ray reading and detection of all areas of the human breast under examination, particularly at all points of connection with the rib cage wall and the axilla area. Furthermore, one such curvature would not be capable of accommodating variations in shape of a rib cage and each breast in patient, as well as variations between individuals with substantially different physical characteristics. Thus, it is desirable to provide an x-ray mammography diagnostic apparatus and method that optimize the curvature of one or more sides of the subject table in such a way as to allow to take a more accurate reading of the left and right breast of an individual under examination, taking into account the different curvature of the breast and the rib cage on each side.

Therefore, there is a need for a simple and inexpensive solution to this problem that would allow a more accurate reading, detection and subsequent diagnosis of all areas of the human breast, particularly at all points of connection with the rib cage wall and in the axilla area.

It is further desirable to improve the accuracy of existing x-ray mammography devices and medical diagnoses based upon the images produced by such devices by providing a full and complete reading of all areas of the human breast and by avoiding significant technological modifications and replacement of thousands of existing x-ray mammography devices and the methods of their manufacturing.

It would be further desirable to improve the accuracy of existing x-ray mammography devices that use removable detector cassettes with photosensitive film, as well as those that utilize a stationary (and removable) digital detector plate as a subject table.

SUMMARY OF THE INVENTION

Accordingly, it is one object of the present invention to provide an x-ray mammography diagnostic apparatus that utilizes a subject table (which also operates as a detector in digital x-ray devices) with at least one side having a concave curved surface that accommodates curvature of the human breast and curvature of the rib cage below the breast to allow a complete x-ray reading and detection of all areas of the human breast under examination, particularly at all points of connection with the rib cage wall and in the axilla area.

It is another object of the present invention to provide an x-ray mammography diagnostic apparatus that utilizes a subject table with at least one side having a concave curved surface that accommodates curvature of the human breast and curvature of the rib cage below the breast and also accounts for differences in breast and body curvature for different individuals, without sacrificing the accuracy of the x-ray readings and detection. It is a further object of the invention to accommodate the natural curvature of the human body in the axilla area, and to allow for a more complete examination and detection of the axilla for metastases.

It is still another object of the invention to provide an x-ray mammography diagnostic apparatus and method that optimize the curvature of one or more sides of the subject table in such a way as to allow individuals with different body proportions to utilize the same device and method and obtain a complete x-ray reading and detection of all areas of the human breast under examination, particularly at all points of connection with the rib cage wall.

It is a further object of the invention that the improved device and method according to the current invention can be incorporated simply and inexpensively into the design for the existing x-ray mammography devices, without significant and extensive changes to their structure or methods of manufacture.

It is still a further object of the invention to provide a more accurate x-ray mammography diagnostic apparatus and method for use in existing x-ray mammography devices that utilize removable detector cassettes with photosensitive film (with or without subject table), as well as with digital mammography devices that use both stationary and removable digital detector plates as a subject table.

In accordance with these and other objects, the present invention provides an optimum curvature for the subject table, which has the concave curved surface(s) on the side(s) of the subject table in order to accommodate curvature of the human breast and curvature of the rib cage below the breast for a complete x-ray reading and detection of all areas of the human breast under examination, particularly at all points of connection with the rib cage wall, as well as in the axilla area. The curvature of the concave curved surface(s) on adjacent or opposite sides of the subject table (or the detector cassette, if used as a subject table upon which subject's breast is placed for examination) each is formed by two or more arcs with different radii and is optimized to allow individuals with different body proportions to utilize the same device and method and obtain a complete x-ray reading with a simple mechanical adjustment, such as a rotation or pivoting of the subject table around an axis. The additional concave curved surface on an adjacent or opposite side of the subject table has a different curvature, and is optimized to fit the curvature of the rib cage below the breast for a complete x-ray reading and detection of both breast areas for each patient, which naturally have different curvature, as well as to accommodate curvature of a human breast and rib cage of individuals with different body proportions.

These and other objectives, characteristics and advantages of the present invention will be disclosed in more detail with reference to the attached drawings.

DETAILED DESCRIPTION OF THE INVENTION

Figure 3:
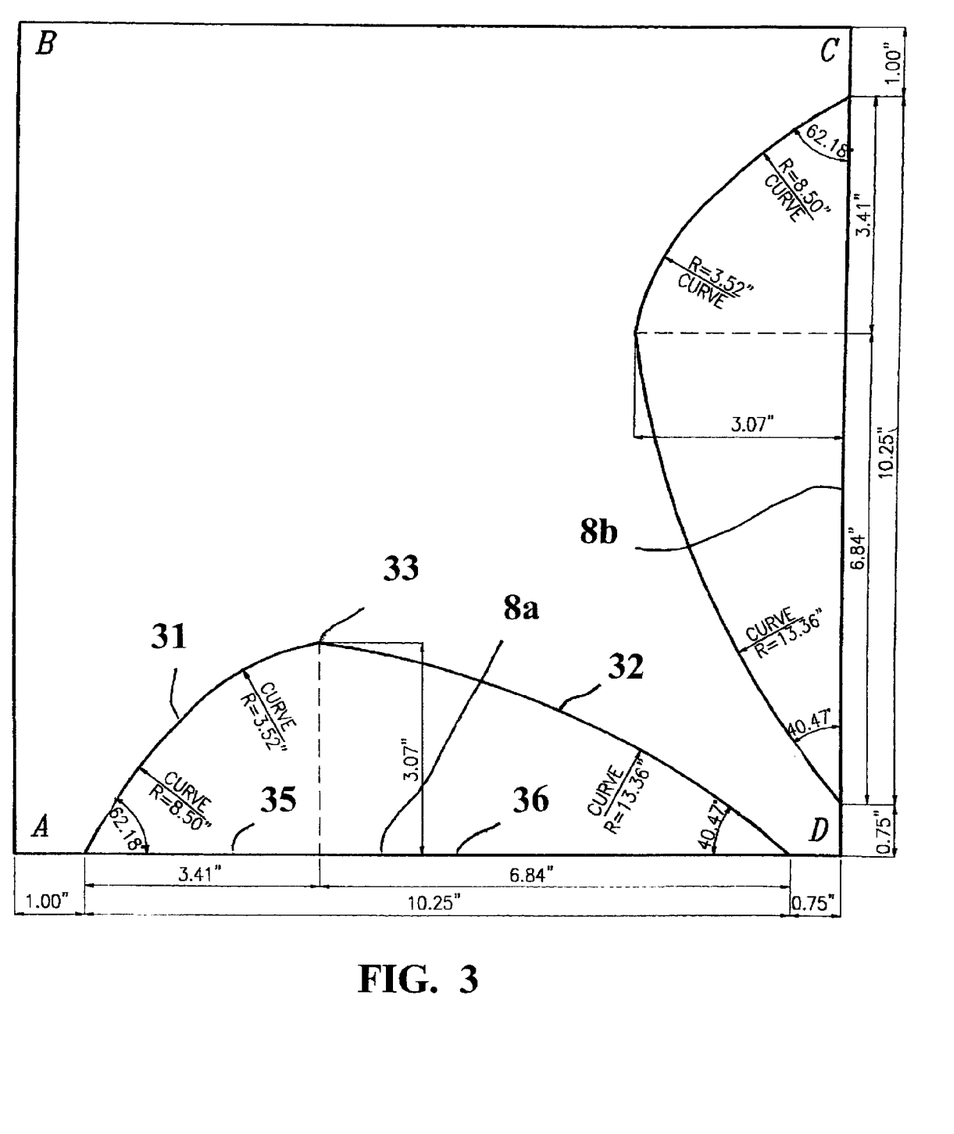
FIG. 3 is a diagram depicting optimized curvature for two adjacent sides of the subject table to be utilized in an x-ray mammography device and method in accordance with the current invention.

In accordance with one embodiment of the current invention, as depicted in FIG. 3, one side 8a of the subject table 8 has a concave curved surface, formed by three arcs 31, 32 and 33 with different curvature and radii. Preferably, there is a 1:2 ratio in the length of the segments 35 and 36 from the corners of the side 8a of the subject table 8 to the point of intersection 34. This particular configuration has been determined to be preferable in that it accommodates curvature of the human breast and curvature of the rib cage below the breast for a large number of subjects, thereby allowing a complete x-ray reading and detection of all areas of the human breast under examination, particularly at all points of connection with the rib cage wall. For those subjects for whom the curvature provided by the concave surface 8a does not provide optimum fit, another concave curved surface 8b is provided on the adjacent side of the subject table 8. In the preferred embodiment, the positions of three arcs 31, 32 and 33 that define the curvature on the 8a are reversed on the adjacent side 8b. The resulting curvature 8b has been determined to be optimal in accommodating the individual with significantly different body proportions, and the two different curvatures for surfaces 8a and 8b are able to accommodate and provide accurate detection for all areas of the breast for most, if not all, individuals, irrespective of their body proportions. The curvatures 8a and 8b also provide for an optimal x-ray detection of cancerous growth and metastases in the axilla area, which is also a naturally curved surface of the human body.

Figure 5:
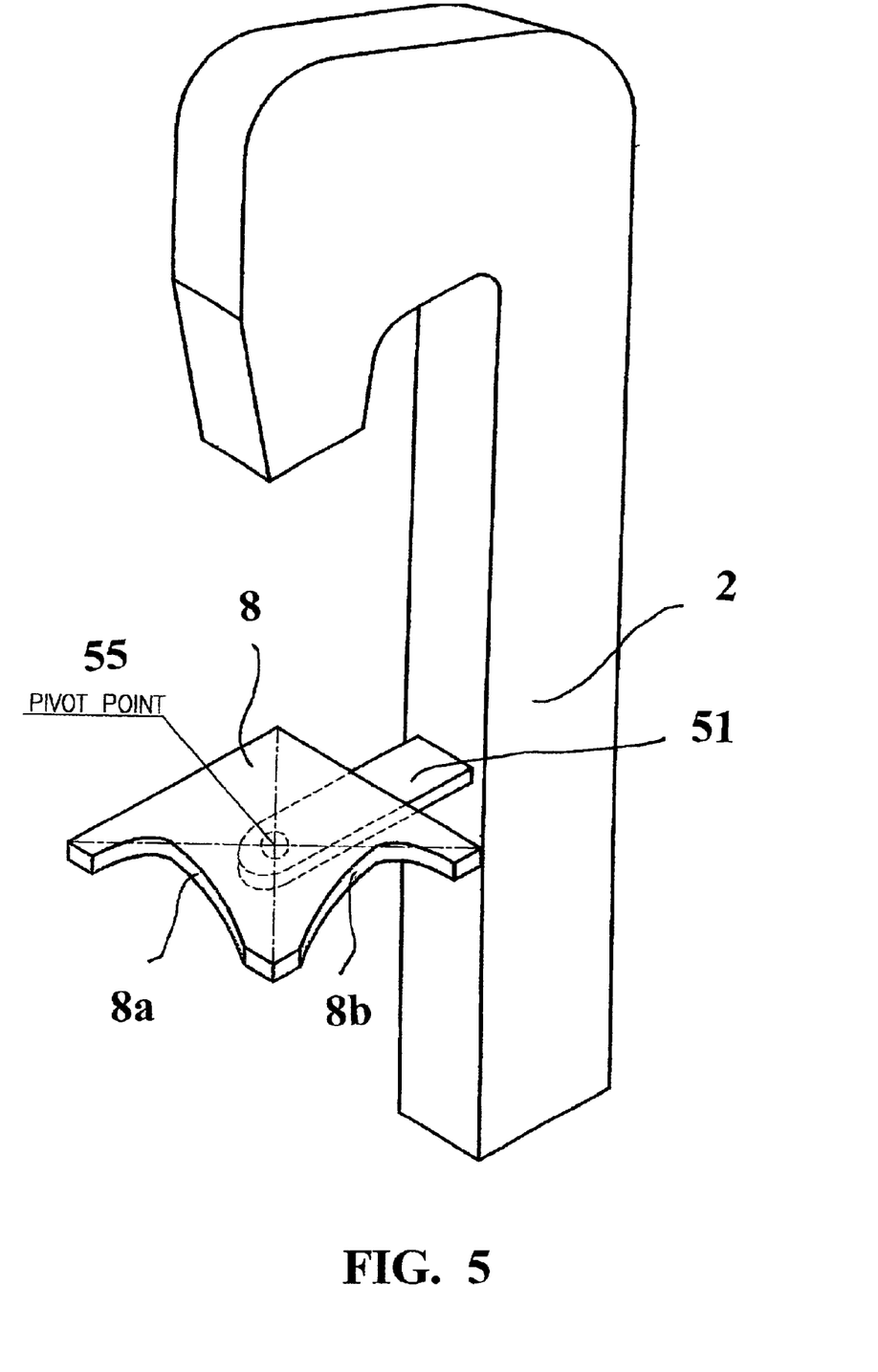
FIG. 5 is a diagram of one particular embodiment of an x-ray mammography device that utilizes a subject table with optimized curvature for two of its adjacent sides in accordance with the current invention.

FIG. 5 illustrates the way the optimally configured subject table with two adjacent concave curved surfaces is incorporated into an x-ray mammography device. The subject table 8, having two concave curved surfaces 8a and 8b that are adjacent to each other is pivotably connected to the housing 2 of the x-ray mammography device 1 by a connecting arm 51, allowing the subject table to pivot laterally around a pivot point 55 (or a vertical axis). Thus, if the curved configuration of one side does not properly accommodate the body proportions of a particular subject, the plate can be easily rotated 45 degrees and the curvature of the adjacent side can be utilized for that individual.

Figure 4:
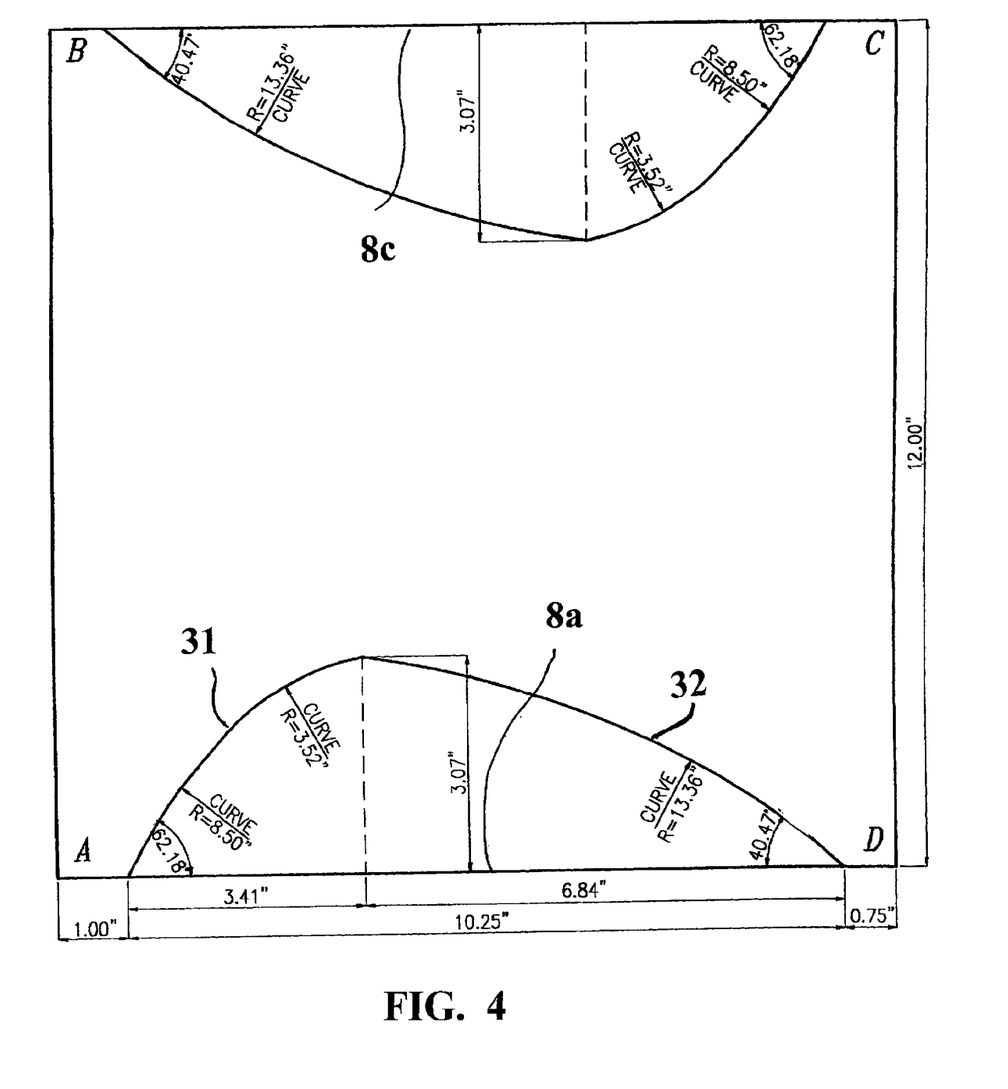
FIG. 4 is a diagram depicting optimized curvature for two opposite sides of the subject table to be utilized in an x-ray mammography device and method in accordance with the current invention.
Figure 6:
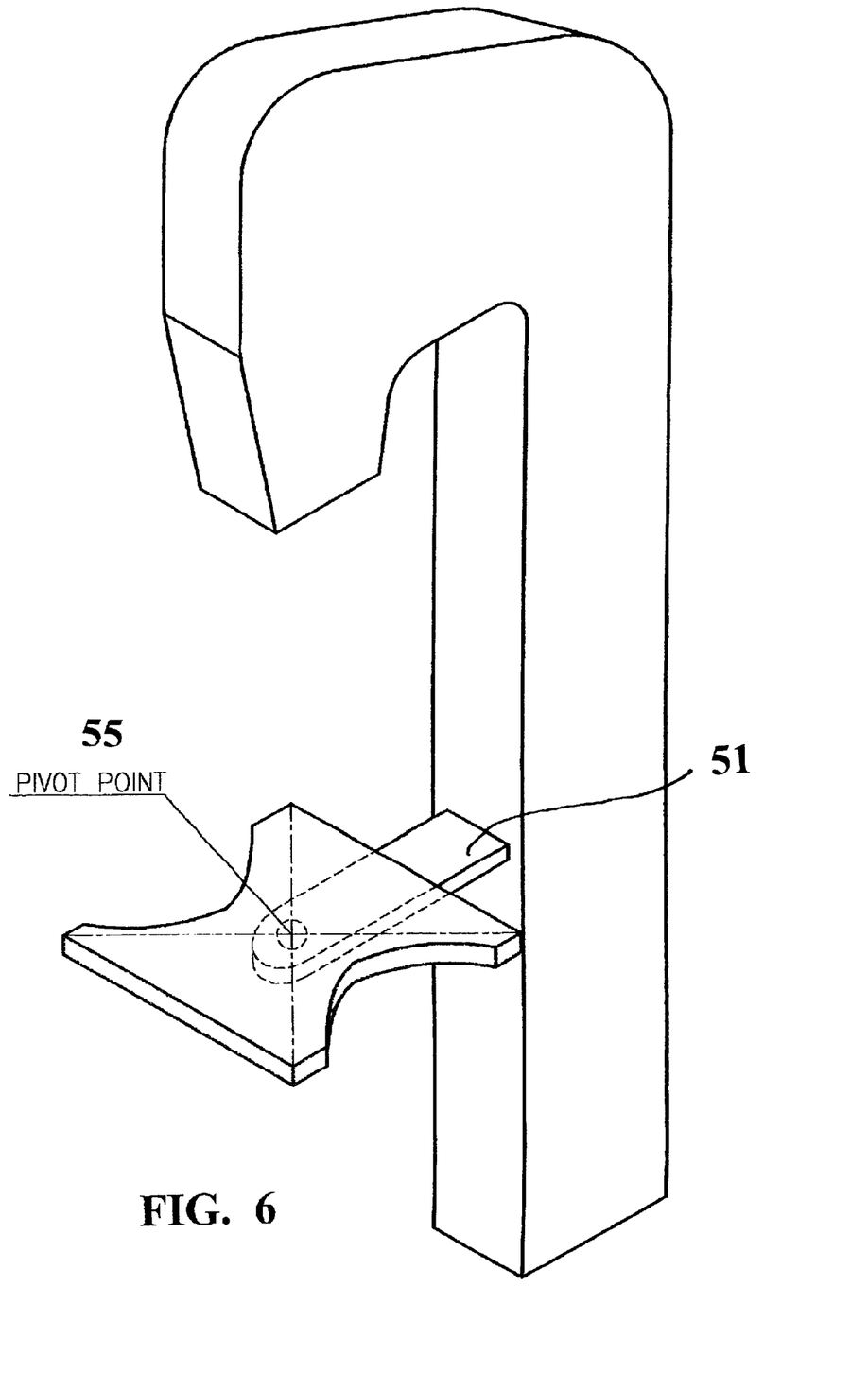
FIG. 6 is a diagram of another embodiment of an x-ray mammography device that utilizes a subject table with optimized curvature for two of its opposite sides in accordance with the current invention.

An alternative embodiment of the current invention is depicted in FIG. 4, where two opposite sides 8a and 8c of the subject table 8 have concave curved surfaces, formed by three arcs 31, 32 and 33 with different curvature and radii, the position of the arcs being reversed on the side 8c in comparison to the curvature on the side 8a. FIG. 6 illustrates the way the optimally configured subject table with two opposite concave curved surfaces is incorporated into an x-ray mammography device. While the description of the preferred embodiments in FIGS. 3, 4, 5 and 6 describes a subject table configured in accordance with the current invention with optimized concave curved surfaces, it is contemplated by the current invention that a removable detector cassette 6, with photosensitive film, may be also configured with concave curved adjacent or opposite sides in accordance with the description above, particularly if the removable detector cassette serves as a subject table upon which the breast is placed during the mammography procedure.

While the fundamental novel features of the invention, as applied to embodiments thereof, have been described and pointed out, it should be understood that various omissions, substitutions and changes in the form and details of the invention, as herein disclosed, may be made by those skilled in the art without departing from the spirit of the invention. It is expressly intended that all combinations of these elements and/or method steps, which perform substantially the same function in substantially the same way to achieve the same results, be within the scope of the invention.

We claim:

1. An improved subject table for use in an x-ray mammography apparatus, said subject table comprising
   a first concave curved surface on at least one side of said subject table, said concave curved surface formed by at least two arcs with different radii, said concave curved surface formed for fittingly accommodating curvature of a rib cane below a human breast under examination;
   a second concave curved surface on at least one other side of said subject table, wherein the second concave curved surface is formed by at least two arcs with different radii, said second concave curved surface having a different configuration than the first concave curved surface, and said second concave curved surface fittingly accommodating curvature of a rib cage below a human breast under examination for individuals with different bodily dimensions than said first concave curved surface.

2. A device according to claim 1, wherein said arcs for the first and second concave curved surfaces are formed by three arcs of different radii, and wherein the first concave curved surface is configured to fittingly accommodate individuals with particular bodily dimensions, and wherein the second concave curved surface is configured to fittingly accommodate individuals with different bodily dimensions.

3. A device according to claim 1, wherein said second concave curved surface is a reversed mirror image of the first concave curved surface.

4. A device according to claim 1, wherein said second concave curved surface is on a side of the subject table that is opposite to the side having the first concave curved surface.

5. A device according to claim 1, wherein said second concave curved surface is on a side of the subject table that is adjacent to the side having the first concave curved surface.

6. A device according to claim 1, wherein said subject table pivots around a vertical axis, whereby allowing to switch from the first concave curved surface to the second concave surface in order to accommodate the particular bodily dimensions of an individual under examination.

7. A device according to claim 1, wherein said subject table pivots around a vertical axis, whereby allowing to switch from the first concave curved surface to the second concave surface and make a complete x-ray reading of a breast and an axilla areas of an individual under examination.

8. A device according to claim 1, wherein a digital detector forms said subject table for examination of the human breast.

9. A device according to claim 1, further comprising a radiation detector.

10. A device according to claim 9, wherein said radiation detector and said subject table are parts of a digital image detector.

11. A device according to claim 1, further comprising a compression mechanism having a compression plate.

12. An x-ray mammography apparatus comprising:
    a housing, carrying an x-ray tube that emits a plurality of x-ray beams;
    a radiation detector for detecting said plurality of x-ray beams emitted by said x-ray tube; and
    a subject table having a first concave curved surface on at least one side, said concave curved surface formed by at least two arcs with different radii, said concave curved surface formed for fittingly accommodating curvature of a rib cage below a human breast under examination;
    said subject table also having a second concave curved surface on at least one other side, wherein the second concave curved surface is formed by at least two arcs with different radii, said second concave curved surface having a different configuration than the first concave curved surface, and said second concave curved surface fittingly accommodating curvature of a rib cage below a human breast under examination for individuals with different bodily dimensions than said first concave curved surface.

13. A device according to claim 12, wherein said arcs for the first and second concave curved surfaces are formed by three arcs with different radii, and wherein the first concave curved surface is configured to fittingly accommodate individuals with particular bodily dimensions, and wherein the second concave curved surface is configured to fittingly accommodate individuals with different bodily dimensions.

14. A device according to claim 12, wherein said second concave curved surface is a reversed mirror image of the first concave curved surface.

15. A device according to claim 12, wherein said second concave curved surface is on a side of the subject table that is opposite to the side having the first concave curved surface.

16. A device according to claim 12, wherein said second concave curved surface is on a side of the subject table that is adjacent to the side having the first concave curved surface.

17. A device according to claim 12, wherein said subject table pivots around a vertical axis, whereby allowing to switch from the first concave curved surface to the second concave surface in order to accommodate the particular bodily dimensions of an individual under examination.

18. A device according to claim 12, wherein said subject table pivots around a vertical axis, whereby allowing to switch from the first concave curved surface to the second concave curved surface and make a complete x-ray reading of a breast and an axilla areas of an individual under examination.

19. A device according to claim 12, wherein said housing is mounted on a horizontal shaft that is rotatably connected to an x-ray stand for rotation about a horizontal axis.

20. A device according to claim 12, wherein said radiation detector comprises a detector cassette with photosensitive film.

21. A device according to claim 20, wherein said detector cassette functions as said subject table.

22. An x-ray mammography apparatus comprising:

an x-ray housing, carrying an x-ray tube that emits a plurality of x-ray beams;

a digital detector having a radiation detector for detecting said plurality of x-ray beams emitted by said x-ray tube and an axially pivoting subject table, having a first and second concave curved surfaces on at least two of its sides, wherein said first concave curved surface formed by at least two arcs with different radii, said first concave curved surface formed for fittingly accommodating curvature of a rib cage below a human breast under examination, and wherein said second concave curved surface is formed by at least two arcs of different radii, said second concave curved surface having a different configuration than the first concave curved surface, and said second concave curved surface fittingly accommodating curvature of a rib cage below a human breast under examination for individuals with different bodily dimensions than said first concave curved surface.

23. A device according to claim 22, further comprising a compression mechanism having a compression plate.

* * * * *